US009050332B2

(12) United States Patent
Häberlein et al.

(10) Patent No.: US 9,050,332 B2
(45) Date of Patent: Jun. 9, 2015

(54) ENZYME CONTAINING COMPOSITION, PROCESS OF PRODUCING SAID COMPOSITION AND ITS USE

(75) Inventors: Ingo Häberlein, Weilheim (DE); Rainer Guggenberger, Herrsching (DE); Wolfgang Weinmann, Weilheim (DE); Oliver Kappler, Weilheim (DE)

(73) Assignee: 3M Innovative Properties Company, St. Paul, MN (US)

( * ) Notice: Subject to any disclaimer, the term of this patent is extended or adjusted under 35 U.S.C. 154(b) by 1248 days.

(21) Appl. No.: 12/122,027

(22) Filed: May 16, 2008

(65) Prior Publication Data

US 2008/0213196 A1 Sep. 4, 2008

Related U.S. Application Data

(63) Continuation of application No. 10/525,294, filed as application No. PCT/EP03/05183 on May 16, 2003, now abandoned.

(30) Foreign Application Priority Data

Aug. 15, 2002 (DE) .................................. 102 37 317

(51) Int. Cl.
  A61K 38/47 (2006.01)
  A61K 38/48 (2006.01)

(52) U.S. Cl.
  CPC ............... *A61K 38/47* (2013.01); *A61K 38/482* (2013.01); *A61K 38/488* (2013.01); *A61K 38/4886* (2013.01)

(58) Field of Classification Search
  CPC ... A61K 38/47; A61K 38/482; A61K 38/488; A61K 38/4886; A61K 2300/00; A61K 6/0017; A61K 6/0029
  See application file for complete search history.

(56) References Cited

U.S. PATENT DOCUMENTS

| 3,940,317 A * | 2/1976 | Katz et al. ................. 435/206 |
| 4,355,022 A | 10/1982 | Rabussay |
| 4,364,926 A | 12/1982 | Yokogawa et al. |
| 4,693,888 A | 9/1987 | Miyahara et al. |
| 4,732,758 A | 3/1988 | Hurion et al. |
| 5,286,405 A * | 2/1994 | Rennie et al. ................. 510/397 |
| 5,386,024 A | 1/1995 | Kacian et al. |
| 5,439,935 A | 8/1995 | Rawlings et al. |
| 5,670,132 A | 9/1997 | Griffiths et al. |
| 6,090,381 A | 7/2000 | Leung et al. |
| 6,105,761 A | 8/2000 | Peuker et al. |
| 6,254,856 B1 | 7/2001 | Tsuchiya |
| 6,287,550 B1 | 9/2001 | Trinh et al. |
| 6,465,236 B1 | 10/2002 | Nishino et al. |
| 6,521,215 B2 | 2/2003 | Okay |
| 6,610,475 B1 | 8/2003 | Kacian et al. |
| 6,752,989 B1 | 6/2004 | Häberlein et al. |
| 7,097,075 B2 | 8/2006 | Peuker et al. |
| 2002/0028251 A1* | 3/2002 | Okay ............................ 424/498 |
| 2003/0211054 A1 | 11/2003 | Szeles et al. |
| 2004/0029171 A1 | 2/2004 | Wagner et al. |
| 2004/0065679 A1 | 4/2004 | Peuker et al. |
| 2004/0071636 A1 | 4/2004 | Delisle |
| 2004/0120901 A1 | 6/2004 | Wu et al. |
| 2005/0265932 A1 | 12/2005 | Kappler et al. |
| 2006/0115436 A1 | 6/2006 | Häberlein et al. |
| 2008/0241122 A1 | 10/2008 | Kappler et al. |
| 2009/0117092 A1 | 5/2009 | Kappler et al. |

FOREIGN PATENT DOCUMENTS

| CN | 1216463 A | 5/1999 |
| DE | 1 944 308 | 3/1971 |
| DE | 100 56 212 A1 | 5/2002 |
| EP | 0 824 910 A2 | 2/1998 |
| EP | 0 895 943 A2 | 2/1999 |
| EP | 0 884 950 B1 | 3/2003 |
| FR | 2 651 433 A1 | 3/1991 |
| GB | 1033229 | 6/1966 |
| GB | 1 265 468 | 3/1972 |
| JP | S48-034897 B | 10/1973 |
| JP | 57-142910 | 9/1982 |
| JP | S58-148828 A | 9/1983 |
| JP | 2-4710 | 1/1990 |
| JP | 03-279330 | 10/1991 |
| JP | 06-172190 | 6/1994 |

(Continued)

OTHER PUBLICATIONS

Gray S.P. et al. Kinetic assay of human pepsin with albumin-bromophenol blue as substrate, Clinical Chemistry, 1983, vol. 29, No. 3, pp. 447-451.*

Pahud J. et al., Calf rennet lysozyme, Biochem. J., 1982, vol. 201, pp. 661-664.*

Banerjee A. et al., Dentine caries excavation: a review of current clinical techniques, British Dental Journal, May 13, 2000, vol. 188. No. 9, pp. 476-482.*

Nordbo H. et al., Chemical treatment of cavity walls following manual excavation of carious dentin, American Journal of Dentistry, Apr. 1996, vol. 9, No. 2, pp. 67-71.*

(Continued)

*Primary Examiner* — Satyendra Singh
(74) *Attorney, Agent, or Firm* — Mueting, Raasch & Gebhardt, P.A.

(57) ABSTRACT

The present invention relates to a composition comprising at least one biologically active protease and at least one biologically active glycosidase wherein the proteases and the glycosidases are present in an activity ratio of from 1,000,000:1 to 1:1,000,000 and wherein the composition has a total enzyme activity of at least 2 U/ml. Furthermore, the present invention relates to a process of producing such enzyme comprising composition and to processes of removing caries. Moreover, the invention relates to the use of one or more enzyme comprising compositions for producing a treatment agent for removing caries.

14 Claims, No Drawings

(56) References Cited

FOREIGN PATENT DOCUMENTS

| | | |
|---|---|---|
| JP | H07-069854 A | 3/1995 |
| JP | H07-157419 A | 6/1995 |
| JP | H11-502527 A | 3/1999 |
| JP | 2001-509535 A | 7/2001 |
| JP | 2001-513139 A | 8/2001 |
| JP | 2002078489 A | 3/2002 |
| RU | 2083215 | 7/1997 |
| WO | WO 92/10165 A1 | 6/1992 |
| WO | WO 96/07329 A1 | 3/1996 |
| WO | WO 97/08669 | 3/1997 |
| WO | WO 97/38669 A1 | 10/1997 |
| WO | WO 98/20838 A1 | 5/1998 |
| WO | WO 98/26807 A1 | 6/1998 |
| WO | WO 00/27204 A1 | 5/2000 |
| WO | WO 01/37787 A1 | 5/2001 |
| WO | WO 02/06820 A2 | 1/2002 |
| WO | WO 02/38468 A1 | 5/2002 |
| WO | WO 2004/000222 A2 | 12/2003 |
| WO | WO 2004/017988 A1 | 3/2004 |
| WO | WO 2004/047782 A1 | 6/2004 |
| WO | WO 2004/060325 A1 | 7/2004 |

OTHER PUBLICATIONS

Eisenberg et al., "Associations of microbiological factors and plaque index with caries prevalence and water fluoridation status," *Oral Microbiol. Immunol.*, 1991; 6:139-145.

Margolis et al., "Composition of Pooled Plaque Fluid from Caries-free and Caries-positive Individuals Following Sucrose Exposure," *Journal of Dental Research*, 1992; 71:1776-1784.

URL<http://en.wikipedia.org/wiki/Dental_caries>, 12 pages [Jan. 14, 2010].

URL<http://en.widipedia.org/wiki/Dental_plaque>, 2 pages [Jan. 14, 2010].

U.S. Appl. No. 10/525,294, filed Sep. 22, 2005, Häberlein et al.

Comellas-Bigler et al., "The 1.4 Å Crystal Structure of Kumamolysin: A Thermostable Serine-Carboxyl-Type Proteinase," *Structure*, Jun. 2002; 10:865-876.

Harrington et al., "Bacterial Collagenases and Collagen-Degrading Enzymes and Their Potential Role in Human Disease," *Infect. Immun.*, Jun. 1996; 64(6):1885-1891.

Lide, "Laboratory Solvents and Other Liquid Reagents," *CRC Handbook of Chemistry and Physics*, 87$^{th}$ Ed., Boca Raton, FL 2006-2007; pp. 15-13 to 15-22.

"Optim Glycerine Viscosity" datasheet [online]. Dow Chemical Company, Midland, MI, 1995-2007 [retrieved on Oct. 23, 2007]. Retrieved from the Internet:<URL:http://www.dow.com/glycerine/resources/table18.htm>; 2 pgs.

Oyama et al., "A CLN2-Related and Thermostable Serine-Carboxyl Proteinase, Kumamoylsin: Cloning, Expression, and Identification of Catalytic Serine Residue," *J. Biochem.*, May 2002; 131:757-765.

Tsuruoka et al., "Collagenolytic Serine-Carboxyl Proteinase from *Alicyclobacillus sendaiensis* Strain NTAP-1: Purification, Characterization, Gene Cloning, and Heterologous Expression," *Applied and Environmental Microbiology*, Jan. 2003; 69(1):162-169.

Wlodawer et al., "Structural and enzymatic properties of the sedolisin family of serine-carboxyl peptidases," *Acta Biochimica Polonica*, 2003; 50(1): 81-102.

Banerjee et al., "In vitro Evaluation of Five Alternative Methods of Carious Dentine Excavation," *Caries Research*, 2000; 34:144-150.

Brännström et al., "Invasion of Microorganisms and Some Structural Changes in Incipient Enamel Caries," *Caries Res.*, 1980; 14:276-284.

Falbe et al., Ed., *Rompp Chemie Lexikon*, 9$^{th}$ Edition, 1995; pp. 3677-3678.

Fejerskov et al., Ed., *Dental Caries: The disease and its clinical management*, "Caries removal and the pulpo-dential complex," Blackwell Munksgaard, Quintessence Books, 2003; Chapter 17.

Heinemann, Ed., *Endodontie*, Urban & Fischer, 2001; pp. 82 and 89.

Kidd et al., "The use of a caries detector dye during cavity preparation: a microbiological assessment," *Microbiology*, Apr. 1993; 174:245-248.

Kneist et al., *Tissue Preservation in Caries Treatment*, "Antibacterial Action of Carisolv™, Caries as an Infectious Disease," Chapter 17, 2001; pp. 205-219.

Paddick et al., "Phenotypic and Genotypic Selection of Microbiota Surviving under Dental Restorations," *Applied and Environmental Microbiology*, May 2005; 71(5):2467-2472.

Perdigao et al., "Field emission SEM comparison of four postfixation drying techniques for human dentin," *Journal of Biomedical Materials Research*, 1995; 29:1111-1120.

Sevgican Figen et al., "Effect of Endodontic Irrigants on Microleakage of Sealers and Restorations," IADR, Poster #2982, 2005; 1 Page.

FDA, Select Committee on GRAS Substances (SCOGS) Opinion: Benzoic Acid. Last Updated Aug. 10, 2011, URL<http://www.fda.gov/Food/FoodingredientsPackaging/GenerallyRecognizedas-SafeGRAS/GRASSubstancesSCOGSDatabase/ucm260036.htm>.

Goshorn, R.H. et al., "Antiseptic and Bartericidal Action of Benzoic Acid and Inorganic Salts, Effect of pH" Industrial and Engineering Chemistry. Jun. 1938, vol. 30, No. 6, 646-648.

Elkholany et al., "Chemo-Mechanical Method: A Valuable Alternative for Caries Removal", Dental News, vol. XI, No. III, 2004, pp. 16-22.

Ullrich et al. "Novel Haloperoxidase from the Agaric Basidomycete Agrocybe aegerita Oxidizes Aryl Alcohols and Aldehydes" (2004) Applied and Environmental Microbiology, vol. 70, Issue 8, 4575-4581.

Tallarida, Ronald, "Drug Synergism and Dose-Effect Data Analysis", Chapman and Hall/CRC, Boca Ratan FL, Chapter 1 and Chapter 4 (2000).

Berenbaum, M., "What is Synergy" Pharmacological Reviews, vol. 1989, No. 41 (1989) pp. 93-141.

Berenbaum, M, "Synergy, additivism and antagonism in immunosupression" Clinical Experimental Immunology (1977), vol. 28, pp. 1-18.

Hoffmann-Axthelm, *Lexicon der Zahnmedizin*, Berlin, Germany 1995, 6. (11.) edition, Statement, cover page, title page and pp. 372-375, 582-585, 808-809.

\* cited by examiner ically active protease or at least one biologically active protease and at least one biologically active glycosidase wherein the proteases and the glycosidases are present in an activity ratio of from 1,000,000 U:1 U to 1 U:1,000,000 U. Furthermore, the present invention relates to a process of producing this enzyme comprising composition and to processes of removing caries. The invention also relates to the use of enzyme comprising compositions for producing a treatment agent for removing caries.
ENZYME CONTAINING COMPOSITION, PROCESS OF PRODUCING SAID COMPOSITION AND ITS USE The present application is a continuation of U.S. patent application Ser. No. 10/525,294, filed Sep. 22, 2005, which is a U.S. National Stage Application of PCT/EP2003/005183, filed May 16, 2003, and which also claims the benefit under 35 U.S.C. §119 of foreign application no. DE 102 37 317.5, filed Aug. 15, 2002. All of the above-identified applications are hereby incorporated by reference in their entirety.

The present invention relates to a composition comprising at least one biologically active protease or at least one biologically active protease and at least one biologically active glycosidase wherein the proteases and the glycosidases are present in an activity ratio of from 1,000,000 U:1 U to 1 U:1,000,000 U. Furthermore, the present invention relates to a process of producing this enzyme comprising composition and to processes of removing caries. The invention also relates to the use of enzyme comprising compositions for producing a treatment agent for removing caries.

Caries which is also called tooth decay is one of the most frequently occuring human diseases. Caries is a bacterial damage of the tooth which may even cause teeth to fall out. From the outside, teeth are protected by a cover of hard enamel enclosing the softer dentin which in turn encloses the so-called pulp. The enamel itself consists of about 95% inorganic compounds, especially hydroxyapatite, and about 5% organic compounds and water. Dentin is softer than enamel and consists of about 65% inorganic compounds (mainly hydroxylapatite), about 20% organic compounds (mainly collagen and polysaccharides) and about 15% water.

A caries disease often starts with the formation of plaque and tartar which develops from plaque. Plaque is a whiteish film on the tooth which mainly consists of a bacteria, proteins, and polysaccharides containing mass which is difficult to wipe off. The term "plaque" describes all microorganisms present on the surface of the tooth and their organic matrix. From plaque, caries and tartar can develop, the latter of which is so damaging to the gums and consists of calcified plaque. Even with careful brushing tartar cannot be removed from the surface of the tooth.

Caries develops in several steps by bacterial fermentation of carbohydrates, in particular by bacterial fermentation of sugar to acids. The acids resulting from said bacterial fermentation firstly dissolve the hard enamel, whereas bacteria attack mainly the organic components such as food particles having remained on the teeth.

If the enamel becomes porous and soft by the bacteria induced influence of acids, bacteria may reach the dentin layer below the tartar and infect it with caries. A caries disease often results in an inflammation of the pulp under the dentin. An inflammation of the pulp is extremely painful and may cause a serious risk to the health of the patient if it is not treated quickly.

The region where the enamel or enamel and dentin are dissolved the most is called the caries lesion. A caries lesion normally consists of a multitude of distinct compounds, partly of bacterial origin and partly coming from saliva as well as from food particles.

Contrary to damages to other living body tissue, there is no endogenous way of repairing tooth damage caused by caries. Only in the early phase of caries healing by means of remineralisation of the hard substance of the tooth is possible. At a later stage of caries there is a need for a treatment, wherein a region of the tooth damaged by caries is removed. The empty space resulting from removing the caries affected tooth tissue is called cavity. Upwards from a certain size of a cavity and after the caries affected tooth tissue has been removed the cavity is normally filled with an artificial filling.

The damages of the tooth caused by caries are normally removed by drilling out the carious tooth tissue with a dental drill. Depending on indication and technique, drill velocities of up to 400,000 rpm are obtained. The drills used are hard metal or diamond instruments. Since drilling causes an enormous release of heat and the removed tooth substances contaminate the site of the treatment, a mixture of water and air is usually required to cool and clean the cavity.

However, this method of treatment for removing caries using a dental drill has several disadvantages.

A serious disadvantage, for example, is that this method of treatment is generally associated with considerable pain for the patient. As pain caused by drilling, the patient feels especially the fine vibrations of the rotating drill instruments at the regions of the tooth which are often inflamed. Additionally there is a whistling drill sound which is perceived as being very unpleasant. Therefore, many patients often wait too long before they have a tooth treated which is affected and damaged by caries.

A further disadvantage regarding this method of treatment is that drilling damages and removes healthy tooth substance. Such a removal of the healthy tooth material, however, is generally undesirable.

A further disadvantage regarding preparation of a tooth infected by caries with a drill is that in spite of drilling out the carious tooth tissue, bacterial residues often remain at the damaged site. Such bacterial residues can give rise to deleterious side effects such as inflammation of the pulp and root of the tooth, the treatment of which is often much more painful than the initial preparatory treatment.

In addition to the classical drilling therapy described above, an increasing number of methods for the gentle treatment of the hard substance of the tooth have been described in the last few years.

WO 98/20838, for example, describes a chemo-mechanical method for removing caries essentially pain-free and without a drill. In order to dissolve caries, the aggressive oxidizing agent sodium hypochlorite is used in combination with amino acids. A disadvantage of this method is that sodium hypochlorite, as a strong oxidizing agent, reacts unspecifically with constituents of infected carious tooth tissue and non-infected healthy tooth tissue.

Furthermore, this method allows only softening of the carious regions at the surface. As soon as the oxidizing effect decreases, the sodium hypochlorite solution must be applied again. Therefore frequent application of the solution is necessary.

Clinical experience demonstrates that the described chemo-mechanical method is very time-consuming and not always successful so that in the end, one nevertheless has to go back to a dental drill.

WO 96/07329 describes a method for treating and preventing caries and paradontosis diseases. It is suggested to fight germs in the oral cavity with enzymes obtained by methods of genetic engineering. Lysozyme and dextranase are mentioned as suitable enzymes. As a starting point for treating and preventing caries, plaque shall be removed with the enzymes. The treatment of caries as such is not mentioned in the document.

Similarly EP 0 824 910 A2 describes the use of certain enzymes for the treatment of plaque. The treatment of caries as such is not mentioned in the document.

WO 92/10165 discloses a composition containing in a certain amount, among other substances, proteases and complexing agents for calcium for removing plaque on prostheses. In this context, proteases working in the neutral or basic environment are preferred. The treatment of caries as such is not mentioned in the document.

WO 97/38669 relates to a composition for avoiding the formation of plaque and for removing plaque, respectively, wherein the composition contains the glycosidases dextranase and mutanase and, optionally, other enzymes such as proteases. It is described that all enzymes used according to the document are applied in the pH range of from 6 to 8. One can use the composition as toothpaste, tooth-powder or irrigation. The treatment of caries as such is not mentioned in the document.

WO 98/26807 describes a method for cleaning and disinfecting surfaces such as working surfaces made from plastics or metal which are coated with a biofilm wherein the used composition contains enzymes. The treatment of caries as such is not mentioned in the document.

The use of lysozyme in combination with the complexing agent EDTA (Ethylene-Diamino-Tetraacetic-Acid) for preventing treatment of caries is described in U.S. Pat. No. 4,355,022. The treatment of caries as such is not mentioned in the document.

Therefore there was a need for a composition with which caries infected tooth tissue can be removed in daily practice in a simple and pain-free manner. Furthermore, there was a need for a composition for removing caries with which the healthy tooth material worth to be preserved is not or not more than avoidable attacked and damaged. Moreover, there was a need for a composition for removing caries which secures that after the treatment of caries essentially no bacterial residues remain. Moreover, there was a need for a method for a pain-free and simple treatment of caries.

Generally, dentists can rely on various methods for the decision, whether a cavity is "clean", i.e., free of carious residues. Very often, however, dentists rely on a distinct acoustic signal being generated by scratching the surface of a freshly prepared cavity with a dental probe. Caries free dentin emits a crisp, clear sound when being scratched with such a dental probe, resulting from a high fraction of mineral material in the cavity walls. While this test is often applied as the most easy way of determining whether a cavity is free of carious material and the reliability of this test is high, it does not necessarily determine exactly the point of removal of tooth material at which the cavity can be defined as being free of caries. Usually, for applying the dental probe method with the desired result, the amount of material to be removed from the tooth is higher than necessary. This can be explained by the fact that slightly demineralized tooth material, which is free of caries bacteria but already partially demineralized, can be treated like healthy tooth material but does not give the typical scratching sound when scratched with a dental probe. It has thus been a long felt need, to have a choice of materials for the removal of caries from a cavity without using a dental drill, which either remove the caries and leave softer, but healthy tooth material basically untouched or remove caries and softened, partly demineralized dental material in order to be able to rely on the dental probe scratch test.

Therefore, it was an object of the present invention to provide a composition with which one or more of the needs described above are fulfilled. It was another object of the present invention to provide a method of treatment for removing caries with which one or more of the needs described above are fulfilled.

Therefore, in a first embodiment of the present invention the invention relates to a composition comprising at least one biologically active protease and at least one biologically active glycosidase wherein the enzyme activity ratios between the proteases and the glycosidases in the composition are in a range of from 1,000,000:1 to 1:1,000,000 and wherein the total enzyme activity is more than 2 U/ml.

An enzyme unit (abbreviated as U) is the respective amount of enzyme which is necessary to convert one µmol of a corresponding enzyme substrate per minute at standard conditions for the respective enzyme. In the case of proteinase K, U relates to the unit mAnson. For the sake of simplicity the abbreviation U is used within the present text also for proteinase K wherein in this case the abbreviation U denotes the unit mAnson. Therefore, in the case of the enzyme proteinase K, the figures of the enzyme activity ratios for the enzyme units (U) are also valid for the enzyme unit mAnson used exclusively for proteinase K.

In the present case, the total enzyme activity [U/ml] relates to liquid as well as pasty and dry products which, for example, consist exclusively of a mixture of enzymes and optionally one or more adjuvants which are also dry.

The enzymes used in the present invention generally can be isolated from plants, animals or fungi as well as from bacteria or yeasts. They may have been produced also via bioengineering. Enzymes are suitable which were isolated from animals, bacteria or yeasts such as enzymes obtained from pig or chicken. Furthermore, also enzymes isolated from the bacterial genus *Streptomyces* or the fungus *Penicillium* or from the bacterial genus *Clostridium*, the fungus *Aspergillus* or *Tritirachium* are suitable. Enzymes are preferred which were isolated from *Streptomyces griseus, Clostridium histolyticum, Aspergillus nidulans, penicillium* species or *Tritirachium album*.

In the context of the present invention, the term "proteases" denotes all enzymes capable of converting proteins proteolytically by hydrolyzing peptide bonds.

The proteases used according to the invention are used for catalyzing the decomposition of protein components which may be present in a caries lesion. For this purpose, generally all proteases are suitable which catalyze protein and peptide degradation. However, in the context of the present invention, those proteases are especially suitable which are capable of catalyzing the decomposition of collagen fibres which are present, for example, in the material of the tooth, or which at least catalyze a change in the structure of the collagen fibres so that the collagen fibres have better solubility characteristics after the protease reaction.

Proteases used according to the invention are, for example, peptidases, peptidyl peptidases, dipeptidases, dipeptidyl peptidases, oligopeptidases, proteinases, endopeptidases, exopeptidases.

A classification of proteases which are suitable according to the invention is also possible with regard to the amino acids or co-factors involved in the proteolytic catalysis. Thus, in the context of the present invention, generally all protease classes such as serine proteases, matrix metalloproteases, aspartate proteases and cysteine proteases may be used. In general, the proteases comprised in the composition shall be used under conditions which allow the respective proteases to catalyze the degradation of the protein components which are present in a caries lesion.

In general, a composition according to the invention may comprise only one protease, but may comprise as well two or more different proteases.

According to one embodiment of the present invention a composition comprises, for example, one protease. According to another embodiment a composition according to the invention comprises about 1 to 10 different proteases, preferably 1 to 6, more preferably 1 to 4 and more preferably 2 to 3 and more preferably 2 different proteases.

According to a preferred embodiment of the present invention a composition comprises at least two proteases. According to an embodiment of the present invention an inventive composition comprises, for example, collagenase and pronase, according to another embodiment a inventive composition comprises, for example, collagenase and proteinase K.

According to another embodiment an inventive composition comprises three proteases, namely collagenase, pronase, and proteinase K. Especially preferred is the use of collagenase from *Clostridium histolyticum* and pronase from *Streptomyces griseus* and proteinase K from *Tritirachium album*. According to another embodiment an inventive composition comprises only one protease, preferably an aspartate protease wherein pepsin and in particular pepsin from pig is preferred.

As glycosidases which can be used in the context of the present invention all those glycosidases are possible which are capable of cleaving and decomposing polysaccharide structures within a caries lesion. In this respect, glycosidases catalyze the hydrolytic cleavage of glycosidic bonds of polysaccharide structures which are present in a caries lesion.

The catalytic mechanism of the glycosidases only works if the respective glycosidase is specifically linked to the substrate. Thus, for example, the lysozyme catalyses the hydrolysis of β-1,4 linkages between N-acetylmuramic acid and N-acetyl-D-glucosamine in polysaccharide structures. In contrast to that, the α-amylase catalyses the hydrolysis of α-1,4 linkages between two D-glucose units in polysaccharide structures and mutanase catalyses the hydrolysis of α-1,3 linkages. The dextranase catalyses the hydrolysis of α-1,6 linkages in dextrane.

In a composition according to the invention, generally all types of glycosidases may be comprised either separately or in combination with other glycosidases, for example α-glycosidases or β-glycosidases or retentive glycosidases or inverting glycosidases.

A composition according to the invention may generally comprise, for example, only one glycosidase, but may comprise as well two or more different glycosidases. According to an embodiment of the present invention the composition comprises, for example, one glycosidase. According to another embodiment the composition according to the invention comprises 1 to about 10 different glycosidases, for example 1 to about 6 or 1 to 4 or 2 to 3, for example 2 different glycosidases.

According to a preferred embodiment of the present invention at least 2 different glycosidases are used in a composition. Preferred glycosidases are lysozyme, α-amylase, mutanase or dextranase or a mixture of two or more thereof. The combined use of lysozyme and dextranase is also suitable. Preferably, at least two different glycosidases are used according to the present invention, in particular lysozyme from chicken egg albumin, α-amylase from *Aspergillus nidulans* and dextranase from *Penicillium* species.

A composition according to the invention is characterized by a distinct relation between the activity of the proteases and the activity of the glycosidases. In general, the enzyme activity ratios of the proteases to the glycosidases in the composition according to the invention are in a range of from 1,000,000:1 to 1:1,000,000.

The above-mentioned activity ratios always relate to the respective standard conditions for the respective enzyme. In this context, the following standard conditions are valid:

pronase: 1 unit corresponds to the conversion of 25 µg of tyrosine per minute at 40° C. and a pH of 7.5 if casein is used as substrate.

collagenase: 1 unit corresponds to the conversion of 1 mmol of L-leucine in 5 h at 37° C. and a pH of 7.5 if collagen is used as substrate.

pepsin: 1 unit corresponds to a ΔE of 0.01 at A280 nm at 37° C. of converted hemoglobin with TCA.

lysozyme: 1 unit produces an activity of 0.001 per minute at a pH of 6.24 and 25° C. As substrate, *M. lysodeikticus* cells are used in a sensing volume of 2.6 ml.

dextranase: 1 unit corresponds to the conversion of 25 µmol of isomaltose per minute at 37° C. and a pH of 6.0 if dextrane is used as substrate.

α-amylase: 1 unit corresponds to the conversion of 1 mg of maltose in 3 minutes at 20° C. and a pH of 6.9 if starch is used as substrate.

proteinase K: 1 Anson unit corresponds to 1 µmol folin positive amino acid at a pH of 7.5 and 35° C. if hemoglobin is used as substrate.

According to the invention, ratios of from about 10,000:1 to 1:1,000,000 or from about 100:1 to 1:1,000,000 or from about 1:1 to 1:1,000,000 or ratios of from about, 1:10 to 1:100,000 or about 1:100 to 1:100,000 between the activity of proteases and the activity of glycosidases are suitable. Especially suitable are, for example, ratios of from about 1:1,000 to 1:100,000, more preferred are ratios of from about 1:3,000 to 1:30,000. Preferred ratios are, for example, of from about 1:100 to 1:500.

The above-mentioned activity ratios explicitly relate to the standard conditions which are valid for the respective enzyme.

Moreover, the present invention relates to a composition comprising a glycosidase and a protease or comprising a glycosidase and at least two or more proteases or comprising at least two or more glycosidases and a protease or comprising at least two or more glycosidases and two or more proteases. A composition according to the invention comprises, for example, about 1 to about 10 glycosidases and about 1 to about 10 proteases, preferably about 6 glycosidases and about 1 to about 10 proteases and more preferably about 4 glycosidases and about 1 to about 10 proteases, more preferably about 2 glycosidases and about 1 to about 10 proteases or about 6 glycosidases and about 6 proteases or about 6 glycosidases and about 4 proteases or about 6 glycosidases and about 2 proteases and more preferably about 4 glycosidases and about 6 proteases or about 4 glycosidases and about 4 proteases or about 4 glycosidases and about 2 proteases and more preferably about 2 glycosidases and about 2 proteases.

According to a preferred embodiment of the present invention a composition according to the invention comprises the proteases proteinase K and collagenase in combination with the glycosidases lysozyme and dextranase.

The present invention also relates to a solution comprising a composition according to the invention and at least one solvent. In general, each solvent in which enzymes can be dissolved without being denaturized can be a component comprised in the composition according to the invention. All aqueous and organic solvents can be used which do not impair the activity of the enzymes to an extent that their use according to the invention is made impossible.

Suitable solvents are, for example, water, linear, branched or cyclic, saturated or unsaturated alcohols with 2 to about 10 C atoms, ketones, esters, carboxylic acids and mixtures of two or more of said types of solvents.

According to the invention, for example dialkyl ketones or alcohols or polymerizable substances of low viscosity such as polyethylene glycol (PEG), hydroxyethyl methacrylate or (2,3-epoxypropyl)methacrylate and mixtures thereof can be used as solvents. Especially preferred alcoholic solvents are methanol, ethanol, isopropanol, and propanol. Other suitable organic solvents are glycerin, dimethyl sulfoxide, tetrahydrofurane, acetone, methyethyl ketone, cyclohexanol, toluene, methylen chloride, chloroform, alkanes and acetic acid alkyl esters, in particular acetic acid ethyl ester.

Generally, it is possible to use the above-mentioned solvents alone or as a mixture of two or more of any of these solvents if the solvent mixtures do not impair the enzyme activity to such an extent that the desired result cannot be obtained. According to a preferred embodiment of the present invention, however, solvent mixtures are used comprising water as a component, in particular aqueous-alcoholic solvent mixtures.

The viscosity of the compositions according to the invention can be essentially within any ranges, from highly fluid to pasty, in case the compositions contain solvent. Often it has turned out to be useful if the compositions have a sufficiently low viscosity in order to flow into regions not easily accessible within a caries lesion to be treated. However, it can also be advantageous if the solvent containing composition according to the invention has a higher viscosity, i.e. if the composition is gel-like so that it does not flow away too quickly when the caries lesion is located at a region at the side of the tooth.

The viscosity ranges of the solution according to the invention are, for example, in a range of from about 1.0 mPa·s to about 1000 mPa·s at +25° C. or, for example, in a range of from about 10 mPa·s to about 100 mPa·s at +25° C.

Generally, all thickening agents which can be used in the present invention can be substances known by the person skilled in the art which are usually employed to adjust the desired viscosity of a solution, if said thickening agents do not or at least not essentially impair the desired purpose of use. Suitable thickening agents are, for example, starch, polyethylene glycol, polyvinyl pyrrolidone, hydroxyethyl propylcellulose, hydroxybutyl methylcellulose, hydroxypropyl methylcellulose, hydroxyethylcellulose, sodium carboxymethylcellulose and inorganic thickening agents such as silica gels or phyllosilicates and mixtures of two or more of the mentioned thickening agents.

The enzyme solutions according to the invention can have, for example, total enzyme activities of from about 2 U to about 1,000,000 U per ml solution. The lower limit is, for example, about 3, 5, 7, or 10 U/ml wherein the inventive effect is normally considerably improved at a lower limit of the total enzyme activity of about 20 or about 25 or about 30 or about 40 or about 45 or about 50 U/ml solution.

Preferably the inventive enzyme solutions comprise about 60 U to about 600,000 U/ml solvent, for example about 100 U to about 400,000 U/ml solvent or about 300 to about 300,000 U/ml solvent or about 500 U to about 200,000 U/ml solvent or about 700 to about 150,000 U/ml solvent or about 1,000 to about 100,000 U/ml solvent or about 5,000 to about 50,000 U/ml solvent. Moreover, in the context of the present description, the described lower limits of the respective ranges can be combined with each of the above-mentioned range limits if the advantageous effect of an inventive enzyme solution occurs especially distinctly within such a range.

The respective enzymes are present, for example, with ratios of 1 U proteases:1 U glycosidases to 1 U proteases:1,000,000 U glycosidases or ratios of about 1 U proteases:10 U glycosidases to 1 U proteases:100,000 U glycosidases or about 1 U proteases:100 U glycosidases to 1 U proteases:100,000 U glycosidases, relating to the standard conditions valid for the respective enzyme. Especially suitable ratios are, for example, of from about 1 U proteases:1,000 U glycosidases to 1 U proteases:100,000 U glycosidases, more preferred are ratios of from about 1 U proteases:3,000 U glycosidases to 1 U proteases:30,000 U glycosidases.

The total protease activity is for example in a range of from about 1 U/ml solvent to about 1,000,000 U/ml solvent, preferably in a range of from about 5 U to about 100,000 U/ml solvent or in a range of from about 50 U to about 50,000 U/ml solvent.

A suitable composition according to the present invention comprising an enzyme combination of two proteases has, for example, the following enzyme activities: collagenase in a range of from about 1 to about 5,000 U/ml solvent, for example about 1 to about 1,000 U/ml solvent or for example about 1 to about 5 U/ml solvent, and proteinase K in a range of from about 10 to about 300 mAnson/ml solvent, preferably about 20 to about 100 mAnson/ml solvent and especially preferably about 20 to about 50 mAnson/ml solvent. Similar concentrations and ratios apply for the combined use of collagenase and a protease different from proteinase K.

Generally, the total glycosidase activity of a composition according to the invention is in a range of greater than 1 U/ml. According to the present invention the total glycosidase activity can be in the range of from about 1 U/ml to about 1,000,000 U/ml solvent, preferably the total glycosidase activity is from about 10 U/ml to about 500,000 U/ml solvent, for example a concentration of from about 50 U to about 300,000 U/ml solvent or a concentration of from about 1,000 U to about 200,000 U/ml solvent or a concentration of about 10,000 U to about 100,000 U/ml solvent.

According to another embodiment of the present invention a composition comprising an enzyme combination of two glycosidases has, for example, the following concentrations:

lysozyme in a range of from 5,000 to 200,000 U/ml solvent, preferably 10,000 to 150,000 U/ml solvent, more preferably 70,000 to 100,000 U/ml solvent, and dextranase in a range of from 10 to 1,000 U/ml solvent, preferably 50 to 500 U/ml solvent and more preferably 90 to 250 U/ml solvent Since a main protein component of a caries lesion is the protein collagen, those solutions are preferred according to the present invention, which alone or in combination with one or more other proteases, are capable of degrading collagen.

According to another embodiment of the present invention an inventive solution for the degradation of structurally intact collagen comprises at least two proteases.

The combined use of, for example, collagenase and another protease such as proteinase K has an advantageous effect on the degradation of structurally native collagen. The degradation of native collagen is induced by the enzyme collagenase. This means that collagenase converts the tertiary structure of the collagen in such a way that after the conversion the secondary structure can also be attacked by other proteases. Collagenase alone, however, is not capable of degrading collagen completely. Proteases such as proteinase K or pronase, however, are not capable of degrading structurally intact collagen. Such proteases can degrade collagen only after a previous reaction of collagen with collagenase. Thus, for an efficient degradation of collagen, a combination of collagenase and other proteases is advantageous.

According to another embodiment of the present invention the selection and the concentrations of the proteases and glycosidases are chosen in such a way that the proteases do not proteolytically inactivate the glycosidases during the period of use.

The higher the mineralisation of the substrate, the more difficult it is for an inventive composition to reach the dentin-collagen. The consequence thereof is that the inventive composition is active and has a degrading effect only there where the substance of the tooth is damaged. Regions of solid substance of the tooth are not attacked by the enzyme containing composition. The effect of an inventive composition comprising a combination of proteases and glycosidases as described above for the treatment of caries or for the use for the preparation of a pharmaceutical preparation for the treatment of caries is controlled by the proportion of mineral substance in the tooth. According to another embodiment of the present invention proteases and glycosidases are used which have a bactericide effect by, for example, degrading components of the cell-walls of bacteria.

Moreover, an inventive composition can comprise at least one buffer or a first compound which when combined with a second compound acts as a buffer. The buffer comprised in an inventive composition serves to adjust the pH value in an inventive solution comprising an inventive enzyme mixture to a value desired for the respective embodiment of the present invention and for preventing a change of the pH value during a defined period of time and for stabilizing the respective solution, respectively.

In the context of the present invention, all customary buffer are suitable, such as phosphate buffer, carbonate buffer, acetate buffer, citrate buffer, tris buffer, glycylglycine buffer or glycine buffer. Sodium phosphate buffer, sodium hydrogen phosphate buffer, sodium dihydrogen phosphate buffer, potassium phosphate buffer, potassium hydrogen phosphate buffer, potassium dihydrogen phosphate buffer or pyrophosphate buffer are preferred. Suitable are also sodium carbonate buffer, potassium carbonate buffer, sodium hydrogen carbonate buffer or potassium hydrogen carbonate buffer. Especially preferably the inventive compositions comprise phosphate buffer and their components, respectively. An especially preferred phosphate buffer is a sodium dihydrogen phosphate buffer.

It is also possible according to the present invention to use buffer systems which not only stabilize the system at the desired pH value but also fulfill a secondary task within the composition, e.g., activate or inactivate the enzyme activity. Thus, also the acids and their salts as described in the following text with regard to their enzyme activating or inactivating properties can be used as buffer systems in order to stabilize the pH value of the present composition. Among those, diethylbarbituric acid, Tricine, glycine-glycine and phosphate buffer are preferred as buffer compounds.

The buffer concentration of a solvent containing a solution according to the present invention can be in the range of up to 100 mol per liter. The concentration mol per liter relates to the acidic fraction in the solution. A range of from about 0.001 to about 10 mol per liter is preferred. According to another embodiment of the present invention an enzyme containing solution comprises a buffer in the range of about 0.001 mol per liter to about 5 mol per liter. The range of from about 0.01 to about 3 mol per liter is preferred, while the range of from about 0.02 to about 2.0 mol per liter is more preferred. According to another embodiment of the present invention an enzyme containing solution comprises a buffer in the range of from about 0.03 to about 10 mol per liter, more preferred in a range of from about 0.05 to about 5 mol per liter and even more preferred of from about 0.08 to 2 mol per liter.

A solution comprising an inventive enzyme mixture generally can have a pH value in the range of about 1 to about 10.

According to another embodiment of the present invention the pH value of an inventive enzyme containing solution is in the range of about pH 5 to about pH 10, in particular of about pH 6 to about pH 9, in particular of about pH 7 or of about pH 1 to about pH 4.

The use of the protease mixtures adjusted to the above mentioned values is advantageous if the proteins in the caries lesion are easily accessible, for example due to a strong demineralization within the caries lesion. If, however, such a solution gets in contact with a mineral material, the proteolytic degradation does not occur. In this way, also a limitation of the effect is achieved by means of a limitation of the availability of substrate. It is an advantage that essentially only infected dentin and dentin which is demineralized to a greater extent is removed, whereas healthy, mineralized dentin is not or only insignificantly attacked. Therefore, the described solutions are very inoffensive towards the healthy material of the tooth at a pH value of about 5 to about 10.

An inventive composition can comprise further adjuvants such as complexing agents, enzyme substrates or enzyme effectors. According to the present invention, enzyme effectors comprise enzyme activators as well as enzyme inhibitors.

In the context of the present invention, complexing agents serve to facilitate the access to the caries lesion by supporting degradation of the hydroxylapatite.

Preferred complexing agents of the present invention are those which form a stable complex with metal ions having a valence of 2. For example, EDTA (ethylen diamino tetraacetic acid), EGTA (ethylene glycol diamino ethyl tetraacetic acid), citric acid or salicylic acid are suitable complexing agents. EDTA (ethylen diamino tetraacetic acid) is the most preferred complexing agent.

In the context of the present invention, further compounds capable of optimizing the ability of the enzymes to function can be added to an inventive composition. Such enzyme activating or inhibiting compounds comprise diethylbarbituric acid, tris(hydroxymethyl)amino methane (TRIS), glycine, glycylglycine, N-(2-acetamido)-2-aminoethane sulfonic acid (ACES), N-(2-acetamido)-imino diacetate (ADA), N,N-bis (2-hydroxyethyl)-2-aminoethane sulfonic acid (BES), N,N-bis(2-hydroxyethyl)glycine (BICINE), 2,2-bis(hydroxyethyl)-imino tris(hydroxymethyl)methane (BIS-TRIS), 2-(cyclohexyl amino)ethane sulfonic acid (CHES), 2-[4-(2-hydroxyethyl-1-piperazine)]ethane sulfonic acid (HEPES), 3-[4-(2-hydroxyethyl-1-piperazinyl)]propane sulfonic acid (HEPPS), 2-morpholinoethane sulfonic acid (MES), 3-morpholinopropane sulfonic acid (MOPS), piperazine-1,4-bis(2-ethane sulfonic acid) (PIPES), N-[tris(hydroxymethyl)-methyl]-2-aminoethane sulfonic acid (TES), N-[tris (hydroxymethyl)-methyl]-glycine (TRICINE), acids such as sulfuric acid, sulfonic acid, phosphoric acid, hydrochloric acid, acetic acid, nitric acid, bases such as sodium hydroxide, potassium hydroxide, lithium hydroxide, ammonia, calcium hydroxide, magnesium oxide, salts such as magnesium chloride, magnesium sulfate, magnesium nitrate, calcium chloride, calcium sulfate, calcium nitrate, iron(III) chloride, iron (II) chloride, ammonium sulfate, sodium chloride, potassium chloride, sodium phosphates, potassium phosphates, manganese salts, cobalt salts, zinc salts, co-enzymes, amino acids, betaine, taurine, sorbitol, xylitol, polyethylene glycol, methylcellulose, mannitol, glycerol and vitamins as well as many other additives known to the skilled person.

The present invention also relates to a process of producing an enzyme containing composition as described in the context of the present invention wherein a suitable selection of enzymes is admixed with a suitable ratio of the respective enzyme activities.

The present invention further relates to a process of producing an enzyme containing composition as described in the context of the present invention wherein suitable adjuvants and one or more suitable solvents are optionally added to a suitable mixture of enzymes.

Regarding producing and storing in an inventive process the person skilled in the art generally can use all known techniques of how to treat enzymes. The composition according to the invention, for example, may be treated by means of chromatography techniques, freeze drying, spray drying, granulation, centrifugation, precipitation, crystallization or ultrafiltration or nanofiltration.

Moreover, all production adjuvants known by the person skilled in the art can be used to improve the storage stability.

The present invention further relates to a process of removing caries wherein the enzyme containing composition as described in the context of the present invention is applied to the region of a tooth affected by caries.

When selecting the suitable treatment solution, in particular when selecting the suitable enzymes for the preparation of a solution for the treatment and removal of caries, one has to consider, for example, which type of caries is present in the particular case.

Generally a difference is made between distinct types of caries. Therefore, for example, caries is classified as broken-down caries with unimpeded access to the dentin, caries lesions wherein carious dentin is still covered with enamel, enamel caries, root caries and root canal caries.

If the spot affected by caries is enclosed with a thick layer of enamel or an old filling and thus is not accessible by the treatment solution, the enamel cover or the old filling may be removed with a fast rotating drill. If, however, the enamel cover is perforated, for example, by an advanced caries disease, it may by penetrated with a composition according to the invention combined with mechanical support without the use of a dental drill. Possible mechanical tools for supporting the penetration of perforated enamel covers comprise a micro-brush with a little brush made of plastics or metal, specimen with a metal tip, specimen with a spoon, specimen with a ball and other tools generally available in a surgery of a dentist for dental use. These tools serve to spread the inventive solution over the site to be treated and to rub said solution in, to remove softened carious dentin and to tactilely make out hard surfaces of dentin and enamel by touch.

If access to the region of the tooth affected by caries is possible, the treatment usually starts with the identification of the carious regions of the tooth in the mouth of the patient. The identification can be carried out by methods known to the dentist, for example by inspection, probing, X-ray, but also by using diagnostic impression materials. The identified, caries infected regions of the tooth are optionally roughly cleaned, for example with a probe or an excavator wherein also abrasion agents may be optionally added. Subsequently the region of the tooth to be treated is rinsed and air-blown.

After these preparations the caries is removed by applying the inventive enzyme containing composition onto the prepared region of the tooth.

The site to be treated as well as the optionally present cavity should always be covered and filled completely with the inventive solution, respectively. A suitable application volume for the treatment of a region of a tooth affected by caries is, for example, about 100 µl. However, the suitable application volume should be adjusted to the particular case, i.e. the size of the cavity and the size of the region of the tooth affected by caries. Therefore, suitable application volumes are in the range of from about 0.001 to about 0.5 ml, preferably in the range of from about 0.01 to about 0.3 ml and more preferably in the range of from about 0.02 to about 0.2 ml.

The preferred exposure time of the inventive enzyme containing composition is in a range of from about 5 s to about 5 min wherein, depending on the size of the caries lesion, the exposure times can be reduced or enhanced. The exposure time is preferably in the range of about 10 s to about 3 min, for example in the range of about 15 s to 2 min or in the range of about 20 s to 1 min.

During the exposure time the carious parts of the caries lesion are degraded, and a larger cavity develops. Once the exposure time has ended, the treated region of the tooth is rinsed and optionally air-blown.

The caries degrading treatment step is carried out, for example, according to the following scheme. A suitable application volume of the enzyme containing solution is applied onto the region of the tooth to be treated, the solution is exposed for about 5 s to about 5 min, and subsequently, the region of the tooth is rinsed with water, for instance. In the following, such a treatment process is referred to as incubation step.

Generally, the incubation step is carried out as often as necessary so that no carious or bacterial residues remain at the treated region of the tooth. The incubation step can be carried out once or more than once, for example twice or three times or even more often. In most cases, however, it will not be necessary to repeat the incubation step more than twice or three times.

In the context of the present invention it has turned out to be especially advantageous when the incubation step is carried out twice in successive steps. The duration of exposure of the inventive enzyme solution to the region of the tooth affected by caries should be about 10 to about 30 s, for example about 20 s.

Therefore, the present invention also relates to a process of removing caries wherein an inventive composition, in particular an inventive composition comprising at least one solvent is applied to a carious region of a tooth.

Furthermore, the present invention relates to a process of removing caries wherein said process is carried out in two or more incubation steps.

Moreover, the present invention relates to a process of removing caries wherein in a first and in one further or several further steps an inventive composition is applied onto the caries region of a tooth.

In the context of the present invention it has turned out that in certain situations it might be advantageous to use an enzyme containing treatment solution which is adjusted to a pH value at which enamel and dentin are attacked and degraded. This, for example, can be the case if the caries lesion is located under a perforated but not completely destroyed enamel cover. In such cases it is possible to remove the enamel cover without a drill by means of an acidicly adjusted enzyme containing treatment solution wherein the enzyme comprised in such a solution induces or carries out the degradation of the carious regions located under the enamel cover.

Furthermore, it may be advantageous if a caries lesion which has been already treated with an enzyme containing composition of a pH value of 5 or above is treated, in an intermediate step or finally, with an enzyme containing treatment solution which is adjusted to a pH value at which the enamel or the dentin are attacked and degraded. Due to the degrading effect of such an acidic solution on dentin and enamel a roughening of the insides of the cavity is achieved thereby preparing and facilitating a subsequent filling therapy.

Suitable treatment solutions have a pH value of less than about 4, in particular less than about 3. Suitable pH values, for example, are within a range of about 1 to about 4, in particular about 1.2 to about 3 or about 1.5 to about 2.5, for example about 2.

Such a treatment solution should comprise at least one enzyme which shows activity at a pH value within the range described above. In this context, the enzyme pepsin is particularly suitable.

According to the present invention, a pepsin solution is described which offers the advantage of preparing a cavity in such a way that the dentist can use his dental probe for evaluating the surface of the cavity walls for complete removal of caries. The treatment with a pepsin solution according to the present invention results in a cavity which has mineralized cavity walls, thus being able to generate the probing sound the dentist is used to. The proteolytic action of the pepsin, combined with the acidic environment of the solution according to the present invention results in an improved removal of collagenoid residues in the cavity. The interaction of proteolytic properties of pepsin and the acidic, mineral dissolving environment of the composition according to the invention is tailor made for this purpose. During the attack on mineral structures of the dentin the acidic portion of the composition according to the invention also denaturates the collagenoid structures, preparing them for the attack of the pepsin. The pH value of the composition in the cavity increases during the treatment due to the dissolution of mineral components in the dentin until the pH value is too high to cause further damage to the mineral components. The enzyme, however, is still active and digests the remaining denaturated proteins in the cavity. Thus, a cavity wall with a composition resembling the healthy dentin is obtained. Such a cavity wall, however, emits the sound dentists are used to, when probing a cavity with a dental probe in order to determine complete removal of carious matter.

The present invention thus also relates to a composition with a pH value of about 2 or less, comprising water, acid, pepsin and a rheological additive, wherein the pepsin is present at a concentration of 1 to 45,000 U/ml and the composition has a viscosity of about 1 to about 1000 mPas.

Generally, a composition as described above can contain any type of acid, organic or inorganic, or mixtures of both types of acids, in order to provide the desired pH value. It has been found to be possible to use organic acids like diethylbarbituric acid, tris(hydroxymethyl)amino methane (TRIS), glycine, glycylglycine, N-(2-acetamido)-2-aminoethane sulfonic acid (ACES), N-(2-acetamido)-imino diacetate (ADA), N,N-bis(2-hydroxyethyl)-2-aminoethane sulfonic acid (BES), N,N-bis(2-hydroxyethyl)glycine (BICINE), 2,2-bis (hydroxyethyl)-imino tris(hydroxymethyl)methane (BIS-TRIS), 2-(cyclohexyl amino)ethane sulfonic acid (CHES), 2-[4-(2-hydroxyethyl-1-piperazine)]ethane sulfonic acid (HEPES), 3-[4-(2-hydroxyethyl-1-piperazinyl)]propane sulfonic acid (HEPPS), 2-morpholinoethane sulfonic acid (MES), 3-morpholinopropane sulfonic acid (MOPS), piperazine-1,4-bis(2-ethane sulfonic acid) (PIPES), N-[tris(hydroxymethyl)-methyl]-2-aminoethane sulfonic acid (TES), N-[tris(hydroxymethyl)-methyl]-glycine (TRICINE) to shift the pH value of a composition according to the present invention into the desired pH range. It has to be noted, however, that some or all of the above-mentioned acids can, besides lowering the pH value, have other effects on the composition, especially acceleratory or inhibitory effects. It is also within the context of the present invention that combinations of the above-mentioned acids are used, wherein one or more acids are added for the purpose of reaching or adjusting a desired pH value and one or more acids are added for other purposes, irrespective of their influence on the pH value.

It has, however, been discovered that inorganic acids such as sulfuric acid, sulfonic acid, phosphoric acid, hydrochloric acid, formic acid acetic acid, propionic acid, citric acid, lactic acid, oxalic acid or nitric acid and the like are advantageous in providing the desired pH value and improving the denaturalizing and mineral dissolving properties of the composition according to the present invention. It has to be noted that in the context of the present invention acids like formic acid and acetic acid are treated as being part of the group of inorganic acids.

It is possible to use combinations of the above-mentioned organic acids with inorganic acids for the purpose of lowering the pH value. It has, however, been found sufficient or even advantageous, if the desired pH value is adjusted by using inorganic acids.

In a most preferred embodiment of the present invention inorganic acids are used for achieving the desired pH range, especially phosphoric acid.

In order to stabilize the pH value of a pepsin containing composition according to the present invention, such a composition can include a buffer system. Generally, buffer systems are known to the skilled person and have to be chosen in relation to the acid used for lowering the pH value. Suitable buffer systems are, e.g., $H_2PO_4/H_3PO_4$, formic acid/formiate, acetic acid/acetate, citric acid/Na-citrate, glycine/HCl.

The buffer concentration preferably lies in the range of about 0.01 to about 2.0 M.

A pepsin containing composition according to the present invention contains at least one rheological additive.

It has been found that dissolved pepsin undergoes a structural change on passing through a pH value of about 3.5 due to configurational and interaction effects around the isoelectric point. Due to those structural and interactional changes pepsin tends to precipitate from the solution on approaching the isoelectric point. This, however, results in a gradual decrease in activity of pepsin on increasing pH values. This behavior, in turn, may be counterproductive to one of the objects of the present invention, namely the removal of collagenous residues in the cavity while leaving the mineral components of the cavity walls basically untouched. It is thus desirable to keep up the activity of pepsin as long as possible and to avoid precipitation of pepsin molecules on approaching the isoelectric point.

It has surprisingly been found, that the addition of rheological additives can inhibit such an early precipitation and facilitate prolonged action of the pepsin even at higher pH values.

As rheological additives, organic thickening agents are successfully used. Suitable rheological additives are polysaccharides. It is thus preferred, when a pepsin containing composition according to the present invention contains a polysaccharide as a rheological additive. Suitable polysaccharides are, for example, starch, mannan, xanthon, alginate, carragen, pectin, polyvinyl pyrrolidone, hydroxyethyl propylcellulose, hydroxybutyl methylcellulose, hydroxypropyl methylcellulose, hydroxyethylcellulose or sodium carboxymethylcellulose and mixtures of two or more thereof. It has to be noted, that the term "rheological additive" and the term "thickening agents" can be used interchangeably in the context of the present text, unless explicitly stated otherwise.

Additionally to the above-mentioned mandatory components water, acid, pepsin and rheological additive, a polyether or a zwitterionic tenside, or a mixture of two or more polyethers and zwitterionic tensides can be present in the pepsin to the containing compositions according to the present invention.

The addition of both types of components has shown to improve the inhibition of precipitation even further. Generally all types of polyethers are suitable for the purpose of inhibiting the precipitation of pepsin. It is a prerequisite, however, that the polyethers used according to the present invention are, at least to a certain extent, water-soluble.

Generally, suitable polyethers should have a solubility in water at a temperature of 20° C. of at least about 1 g/l, preferably more, e.g., at least about 5 or at least about 200 g/l. It is preferred, if polyethers used as a constituent of the compositions according to the present invention exhibit a solubility in water at a temperature of 20° C. of at least about 0.1 wt.-%, preferably at least about 1 wt.-% or at least about 2 wt.-%.

Suitable polyethers are generally made by reacting a starting material, usually water, alcohol or amine, with one or more epoxides in a base catalyzed, ring opening reaction. It is also possible to obtain suitable polyethers by ring opening polymerization of cyclic ethers like tetrahydrofuran (THF) Preferred starting materials are water or mono- or polyfunctional alcohols. Suitable monofunctional alcohols are linear or branched, saturated or unsaturated aliphatic, cycloaliphatic or aromatic alcohols with 1 to about 22 carbon atoms. e.g., methanol, ethanol, n-propanol, isopropanol, n-butanol, isobutanol, tert-butanol, the isomeric pentanols, the isomeric hexanols, the isomeric heptanols and their higher homologues, cyclohexanol, phenol, naphthol and the like. Among the preferred polyfunctional alcohols are alcohols with 2, 3 or 4 hydroxyl groups, e.g., ethylene glycol, propylene glycol, butylene glycol, trimethylolpropane, triethylolpropane, pentaerythritol, sorbitol and the like.

Suitable epoxides or cyclic ethers in general are oxirane (ethylene oxide), propylene oxide, butylene oxide or THF.

Polyethers, which exhibit an inhibitory effect on the precipitation of pepsin according to the present invention can comprise only one type of monomers. It is, however, also within the scope of the present invention to employ polyethers which are comprised of more than one type of monomer. Such copolymers can be organized randomly or in blocks.

It is preferred within the present invention to employ a polyether which is mainly or completely comprised of ethylene oxide repeating units (—$CH_2$—$CH_2$—O) and has two or three hydroxyl groups.

The weight average molecular weight (Mw) of such polyethers, as measured by conventional methods like GPC, should not exceed about 10,000 atomic units, preferably it should be less than about 1,000 atomic units. The minimum weight average molecular weight (Mw) of such polyethers should be about 100 atomic units, preferably 150 atomic units or more, e.g. about 200 atomic units.

According to a preferred embodiment of the present invention, a pepsin containing composition contains polyethylene glycol with a molecular weight of about 100 to about 500 atomic units, preferably 200 atomic units.

Instead of or additionally to one or more of the abovementioned polyethers, a pepsin containing composition according to the present invention can contain one or more zwitterionic compounds. Generally, all types of low molecular components bearing at least one positively charged ion and one negatively charged ion are suitable in the present context. The term "low molecular" relates to zwitterionic components with a molecular weight of less than about 1000, preferably less than about 500. In a preferred embodiment of the present invention, a pepsin containing composition according to the present invention contains one or more of the the following components as a zwitterionic compound, glycine betaine, betaine, taurine, ectoines or dimethylsulfonium propionate.

Furthermore, a pepsin containing composition according to the present invention can contain one or more polyhydric alcohols with four or more hydroxyl groups which are not polyethers. Suitable polyhydric alcohols or sugar alcohols like are pentaerythritol, xylite, sorbitol, glucose, sucrose, fructose, mannitol or glycerol.

Since proteases themselves are proteins, a protease containing solution is always in danger of losing its reactivity due to self digestion of the enzymes in the solution. Especially pepsin containing solutions which are stored at pH values of less than 4 can undergo a rapid decrease in activity. In order to delay this decrease in activity, an inhibitor can be added to such a solution. While this inhibitor delays the self digestion of pepsin in the solution, it also slows down the reactivity towards proteins in a cavity. It may, however, be desirable to have a solution with an increased storage stability for the sacrifice of reactivity towards caries. A pepsin containing composition according to the present invention can thus furthermore contain an inhibitor.

Suitable inhibitors can be the inhibitors already mentioned above. Preferred inhibitors are polylysin, pepstatin A or substituted piperidines.

The pepsin containing compositions according to the present invention generally contain pepsin in an amount of about 1 to about 100,000 U/ml of composition. It is, however, preferred, if the activity of the pepsin is about 500 to about 50,000 U/ml of composition or about 1000 to about 8000 U/ml of composition. The desired activities can be obtained, e.g., by adding an amount of about 0.5 to about 15 mg of pepsin of an ordinary, commercial available quality per ml composition.

The rheological additive is added in an amount sufficient to provide for a viscosity of about 1 to about 1000 mPas. It is preferred, if a composition according to the present invention has a viscosity of about 5 to about 500 mPas or about 10 to about 100 mPas.

The viscosity is measured according to standard procedures with a Haake rheometer (Rotor-Visco (RV1); sensor (60/1° Ti) at 25° C.

A pepsin containing composition according to the present invention contains a rheological additive in an amount of about 0.1 to about 2 wt.-%, based on the weight of the composition. It is preferred, when the amount of rheological additive is in a range of about 0.2 to about 1 wt.-%, provided that the viscosity of the composition is within the above-mentioned range.

The pepsin containing composition according to the present invention can contain a polyether or a mixture of two or more polyethers in an amount of about 0.1 to about 20 wt.-%, based on the weight of the composition. It has, however, been found to be advantageous if the polyether is present in an amount of about 0.5 to about 8 wt.-%, especially in an amount of about 0.8 to about 5 wt.-%.

If the pepsin containing composition according to the present invention contains a zwitterionic compound or a mixture of two or more zwitterionic compounds, such components are present in an amount of about 0.1 to about 20 wt.-% based on the weight of the composition.

Generally, it has been found to be advantageous if zwitterionic components are present in an amount of about 1 to about 15 wt.-% or about 7 to about 12 wt.-%.

A pepsin containing composition according to the present invention can additionally contain preservatives. Generally, all types of preservatives can be used as part of the compositions according to the present invention which inhibit the growth of microorganisms in a solution according to the present invention and which are tolerated by the human body. It has, however, been found that conventional preservatives of the para hydroxy benzoic acid ester type are most preferred. Especially preferred are preservatives known under the names methyl para hydroxy benzoic acid ester (methylparabene) and propyl para hydroxy benzoic acid ester (propylparabene). Each of the named preservatives can be used as the sole preservative in a composition according to the present invention. It is, however, also possible to use combinations of such preservatives. The preservatives are generally used in an amount of about 0.001 to about 1 wt.-%, based on the weight of the composition. In a preferred embodiment of the present invention, preservatives I used in an amount of about 0.01 to about 0.25 wt.-%, based on the weight of the composition.

Furthermore, the pepsin containing compositions according to the present invention can contain other additives such as complexing agents, enzyme substrates or enzyme effectors, as have been described in the present text above.

In order to overcome the problems related to storage stability and loss of activity of pepsin containing solutions according to the present invention it has been found that such pepsin containing solutions can be advantageously provided in the form of a two component system.

The present invention thus also relates to a composition comprising two components A and B, wherein component A comprises water, a buffer system providing for a pH value above the pH value at which pepsin is most active and a rheological additive and component B comprises water, an acid providing for a pH value of less than or equal to the pH value at which pepsin is most active, a thickener and a polyether or a zwitterionic tenside or a mixture of polyethers and zwitterionic tensides.

The pepsin containing composition according to the present invention can thus also consist of two components A and B. Component A comprises water and a buffer system providing for a pH value above the pH value at which pepsin is most active. Generally, suitable buffer systems will provide for a pH value of about 3.5 or more, especially about 4 or more or about 4.5 or 5 or more. It has been found to be especially helpful, if component A has a pH value of more than about 5.2, especially more than about 5.3 or more than about 5.4. A pH value of about 5.5 has been found to give very good results.

The term "buffer system", as used in the present text, relates to a system being able to provide a buffering effect with regard to component A as well as a mixture of components A and B. it is thus not generally necessary, that component A contains a complete buffer system. It is sufficient, if a mixture of components A and B results in such a buffer system.

Generally, all types of buffer systems can be used, as described in the text above. In a preferred embodiment of the present invention a phosphate buffer is used. Component A preferably contains a phosphate buffer at a pH value of about 4.5 to about 6. It has been found to give good results, if component A contains phosphate buffer in a concentration of about 10 to about 500 mmol/l, especially about 50 to about 150 mmol/l.

In a composition according to the present invention, component A preferably contains a pepsin activity of less than about 60,000 U/ml, especially about 500 to about 50,000 or about 5,000 to about 45,000 U/ml composition. Generally, the remarks with regard to pepsin concentration and activity as described in the above text, also is valid for the presently described composition.

Component A generally contains less than about 20 mg pepsin/ml of component A, preferably less than 15 or less than 10 mg/ml of component A.

Components A further contains a rheological additive. Suitable are, e.g., the rheological additives as already described above. In a preferred embodiment of the present invention, component A contains a polysaccharide as a rheological additive, e.g., hydroxyethylcellulose. Rheological additives can be present in component A in an amount of about 0.05 to about 1.5 wt.-%, preferably in an amount of about 0.1 to about 1 wt.-% or about 0.3 to about 0.7 wt.-%.

In a preferred embodiment according to the present invention, component A can contain the following constituents in the following amounts:

| | |
|---|---|
| pepsin: | about 0.1 to about 1.0 wt.-% |
| sodium dihydrogenphosphate: | about 0.6 to about 2.4 wt.-% |
| sodium hydroxid: | about 0.001 to about 0.5 wt.-% |
| hydroxyethylcellulose: | about 0.2 to about 1.0 wt.-% |
| methylparabene: | about 0.005 to about 0.05 wt.-% |
| propylparabene: | about 0.005 to about 1.0 wt.-% |
| water: | ad 100 wt.-% |

Component B according to the present invention comprises water, an acid providing for a pH value of less than 4.0, a thickener and a polyether or a zwitterionic tenside or a mixture of polyethers and zwitterionic tensides Generally, component B can contain all types of acids which have been mentioned above for reaching a desired pH value. Since components A and B can form a buffer system after mixing, it can be advantageous if at least one acid in component B matches a salt contained in component A. In a preferred embodiment of to the present invention component B contains phosphoric acid. It has further been found to be advantageous, if component B contains the acid in such an amount that a pH value of 1 to about 2.8, especially about 1.5 to about 2.5 is reached.

Component B further contains a polyethyleneglycol or a zwitterionic compound or both. As polyethylene glycols, the above mentioned polyethylene glycols are suitable. It is preferred, to use polyethylene glycol was in the above specified range of molecular weights. If component B contains polyethylene glycol, the amount is within the range of about 0.1 to about 10.0 wt.-%, preferably about 0.5 to about 5.0 wt.-%, based on the weight of component B.

If component B contains the zwitterionic compound, the above-mentioned zwitterionic components are preferred. The amount of zwitterionic compounds in component B is in range of about 0.1 to about 20 wt.-%, especially about 1 to about 15 or about 7 to about 12 wt.-%.

In a preferred embodiment according to the present invention, component B can contain the following constituents in the following amounts:

| | |
|---|---|
| sodium dihydrogenphosphate: | about 10 to about 20 wt.-% |
| phosphoric acid: | about 5 to about 10 wt.-% |
| polyethylene glycol: | about 2 to about 5 wt.-% |
| hydroxyethylcellulose: | about 0.2 to about 1.0 wt.-% |
| water: | ad 100 wt.-% |

Component A and component B can contain one or more of the above-mentioned additives. Preferably one of components A or B contains at least one colorant in order to be to discriminate between the components and to be able to determine whether the components were thoroughly mixed before application.

The ratio in which components A and B are mixed, largely depends on the desired properties of the mixture. Generally, the components must be mixed in such a way that the pH value of the mixture is below the pH value of component A. Preferably, the ratio is chosen such that the properties of the mixture correspond to the properties described above for the pepsin containing composition. It is thus preferred, when components A and B are mixed in a ratio which leads to a mixture having a pH value of less than about 4, preferably less than about 3.8 or less than about 3.5, especially preferred less than about 3.3 or less than about 3.2.

It is further preferred, when a mixture of components A and B has the following properties:

| | |
|---|---|
| pH value: | about 1.5 to about 3.5 |
| viscosity: | about 10 to about 50 mPas |
| pepsin activity: | about 1,000 to about 10,000 |
| buffer capacity: | about 0.5 to about 2.0 |

Components A and B are advantageously prepared such that in order to arrive at a mixture for application with the above-mentioned properties the ratio of components A and B is about 5:1 to about 1:5, especially about 2:1 to about 1:4 or about 1:1 to about 1:3.5, preferably about 1:2 to about 1:3.

The present invention also relates to a process of removing caries wherein a treatment solution as used which comprises at least one protease having its proteolytic catalytic action optimum at a pH value of about 5 or less or at a pH value of about 4 or less.

Furthermore, the present invention relates to a process of removing caries wherein a caries lesion is contacted with at least one composition according to the present invention and with at least one treatment solution comprising a protease having its proteolytic catalytic action optimum in an acidic pH range of below 7.

According to another embodiment of the present invention such a treatment solution comprises, for example, an aspartate protease, preferably pepsin. The starting pH value of the treatment solution used in this process is preferably about 1.0 to about 2.5. Such a treatment solution used in the context of the present invention preferably comprises a buffer.

A further embodiment of the present invention relates to the process for the treatment of caries, wherein two components A and B as described above are mixed and a caries lesion is contacted with this mixture.

A further embodiment of the present invention relates to the use of the mixture comprising components A and B, wherein component A comprises water, a buffer system providing for a pH value above the pH value at which pepsin is most active and a rheological additive and component B comprises water, an acid providing for a pH value of less than the pH value at which pepsin is most active, a thickener and a polyether or a zwitterionic tenside or a mixture of polyethers and zwitterionic tensides, for the treatment of caries.

A further embodiment of the present invention relates to the use of the composition comprising components A and B, wherein component A comprises water, a buffer system providing for a pH value above the pH value at which pepsin is most active and a rheological additive and component B comprises water, an acid providing for a pH value of less than the pH value at which pepsin is most active, a thickener and a polyether or a zwitterionic tenside or a mixture of polyethers and zwitterionic tensides, for the preparation of a pharmaceutical product which is useful for treatment of caries.

The caries treatment process with such a treatment solution preferably comprising pepsin is carried out essentially according to the process already described in which a composition according to the invention is used.

A respective acidic treatment solution may provide access to the minerally coated protein parts in a caries lesion via an already porous enamel cover. At the same time the acid denaturizes the proteins in the caries lesion. In this way the proteolytic degradation is supported. This is advantageous particularly for the high collagen proportion because native and structurally intact collagen is only slowly attacked by pepsin. Acid and pepsin have a synergistic effect in this case.

In order to prevent the composition described herein from penetrating too deeply into the tooth and thereby also damaging healthy tooth material, use is made of the alkaline property of the hydroxyapatite. The more hydroxyapatite is dissolved, the further the pH value of the solution is shifted towards pH 5.5 which limits the hydroxyapatite dissolving capacity of the acidic pepsin solution. Therefore, the acidic pepsin containing solution is not dangerous for healthy regions of the tooth. Furthermore, it is advantageous that the acidic pepsin solution has a germ killing effect.

In the context of the present invention, the described treatment solution can be used alone in one or more subsequent steps for treating caries lesions. According to the invention, however, it is also possible to use the treatment solution in combination with a composition according to the invention, especially in combination with a solvent comprising composition according to the invention.

Generally, the sequence of treatment steps with a composition according to the invention and an acidic treatment solution is essentially arbitrary. Thus, the composition according to the invention and the acidic treatment solution can be used, for example, in 2 or more steps alternately or several times in succession one after the other in each case. Thereby, the first treatment step can be carried out with a composition according to the invention or with an acidic treatment solution.

Preferably a rinsing step takes place between the separate treatment steps wherein the residues of the dissolved parts of the caries lesion are removed together with the composition used for the treatment or with the treatment solution.

The present invention also relates to a process for removing caries wherein a caries lesion is contacted with at least one composition according to the invention and at least one treatment solution comprising at least one protease having its proteolytic catalytic action optimum in an acidic pH range of below 7. Preferably, the treatment is carried out in two or more subsequent steps.

According to an embodiment of the present invention it has turned out to be advantageous, for example, when at first two incubation steps are carried out with a solution according to the invention and a final incubation step is carried out with the acidic treatment solution. The acidic treatment solution slightly etches the surface of the tooth, thus consequently being well suitable for the preparation of a filling therapy following the caries removement. Due to the hard and somewhat rough surface resulting from the etching effect of the acidic treatment solution the filling materials adhere very well to the tooth.

According to a further embodiment of the present invention it has turned out to be advantageous when the first incubation step is carried out with an acidic pepsin containing solution. This approach is optimal in the case of a tooth damage where the enamel layer covers the infected dentin but where said enamel layer has become porous and soft due to caries to such an extent that the acid is sufficient to provide an access to the dentin through the porous enamel layer, to denaturize collagen and to degrade denaturized collagen.

Thereafter, for example, an incubation step with a solution according to the invention can be carried out in order to degrade the denaturized collagen.

It is an effect of the process of treating caries according to the present invention that essentially no detectable caries active bacteria remain at the region of the tooth previously affected by caries. This is proved, for example, by microscopic analyses.

The solutions for the treatment of caries proposed according to the invention can be provided for the end user generally in any facultative form. In the basic form a kit can be provided for the user which comprises two or more of the above mentioned enzymes which then are mixed by the user himself in the necessary amount.

Therefore, the present invention also relates to a kit comprising at least two enzymes being capable of being admixed to obtain a composition according to the invention.

In order to facilitate the mixing process for the user it can be advantageous to add a suitable solvent to the kit. Moreover, it is absolutely possible and facilitating the application if the enzymes comprised in the kit are already present admixed in a suitable mixing ratio with regard to their activity within the above mentioned limits.

Often it makes sense to combine the treatment with a composition according to the invention and an acidic treatment solution. In order to facilitate the application for the user also in this case it turned out to be advantageous when the composition according to invention and the acidic treatment solution are provided as a kit as well.

Therefore, the present invention also relates to a kit comprising at least one composition according to the invention or at least one acidic treatment solution comprising at least one protease having its proteolytic catalytic activity optimum in an acidic pH range of below 7, or comprising at least one composition according to the invention and at least one acidic treatment solution comprising at least one protease having its proteolytic catalytic activity optimum at a pH value of about 4 at most.

When the composition according to the present invention is provided in two components, the components can generally be provided in any type of package, e.g., tubes, flasks and the like. For the application of small amounts of liquids, however, the prior art discloses a number of alternatives which facilitate the application of such small amounts of liquid especially in dental applications, where restricted operating space often leads to difficult handling of simple applicators.

According to the present invention it is thus preferred, to supply the above mentioned compositions with two components A and B in a technically more advanced package which facilitates mixing and application of the two components. According to the other preferred embodiment of the present invention, the two components A and B are supplied in multi chamber applicators as described in WO 02/06820 on pages 3 to 4 and 13 to 17 and FIGS. 1 to 4, DE 100 56 212 A1 column 2 to 10 and FIGS. 1 to 5 and U.S. Pat. No. 6,105,761 column 2 to 5 and FIGS. 1 to 6, respectively. The above mentioned documents are explicitly mentioned and their disclosure, especially the disclosure relating to dispensing devices for multi component compositions disclosed in the above mentioned locations is regarded as being part of the disclosure of the present invention.

The present invention thus relates to a multi chamber device for storing and dispensing liquids, characterized in that at least one chamber contains a component A and at least one chamber contains a component B, wherein component A comprises water, a buffer system providing for a pH value above the pH value at which pepsin is most active and a rheological additive and component B comprises water, an acid providing for a pH value of less than the pH value at which pepsin is most active and, a rheological additive and a polyether or a zwitterionic tenside or a mixture of polyethers and zwitterionic tensides.

The present invention further relates to the use of at least one protease having its proteolytic catalytic activity optimum in the acidic pH range of below 7, especially at a pH value of 4 at most, for producing a treatment agent for removing caries.

The invention is described in more detail in the following examples.

EXAMPLES

Enzymes Used:

The enzymes pepsin, collagenase, lysozyme, pronase, dextranase, and alpha-amylase were purchased from the company SIGMA. The enzyme proteinase K was purchased from the company ICN.

Example 1

Formulations

| | Solution 1: | |
|---|---|---|
| | name | Concentration |
| enzyme | lysozyme | 88,000 u/ml |
| | dextranase | 110 u/ml |
| | collagenase | 2.7 u/ml |
| | proteinase K | 38 mAnson/ml |
| buffer | sodium dihydrogen phosphate | 0.025 mol/l pH 7.0 |
| solvent | water | |
| adjuvants | carboxymethyl cellulose | 2% |

| | Solution 2: | |
|---|---|---|
| | name | concentration |
| enzyme | pepsin | 1 mg/ml |
| buffer | sodium dihydrogen phosphate | 1 mol/l pH 2.0 |
| solvent | water | |
| adjuvants | HEC | 0.5% |
| | PEG 200 | 3% |

Example 2

Treatment Process

The examinations as to the determination of the efficiency of the solutions according to the invention were carried out in vitro with extracted carious teeth.

1. Access

If necessary, the part of the enamel layer covering the carious region was removed by a fast-rotating drill.

2. Optionally Rough Cleaning

Rough cleaning is not necessary, facilitates, however, the examination of the effect of the treatment for the dentist. With an excavator or a caries spoon the rough cleaning of the caries lesion was performed.

3. Treatment with Enzyme Solutions
a) 20 s 100 µl of solution 1
b) rinsing
c) 20 s 100 µl of solution 1
d) rinsing
e) 20 s 100 µl of solution 2
f) rinsing
g) thereafter optionally filing therapy Since both solutions are each capable of making the region of the tooth affected by caries free of bacteria, a treatment can be carried out also with exclusively either solution 1 or 2 or also in different sequence. A combined use is preferred. A final application of the acidic solution 2 (pH value 2.0) is especially advantageous if subsequently a filling therapy is intended.

Example 3

Proof of Absence of Bacteria

After the enzyme solution for removing infected hard substance of the tooth in the caries lesion had been applied in accordance with the requirements, the extracted and treated tooth was air-blown and fixed in an embedding mass (cytofix, Struers company). With an internal hole saw, tooth sections through the caries lesions were made step by step. The tooth sections were freed from covering embedding material and each incubated in 1 ml live/dead dye solution for bacteria (Live/Dead BacLight, Molecular Probes company). During incubation the tooth sections were stored protected from light. With a fluorescence microscope (Zeiss company, Axioplan 2) the marked bacteria were studied under reflected light with a 24 FITC filter at an enlargement factor of 630 and 1000. While in an untreated sample under the same conditions a bacteria bed was observed, the samples treated according to the invention were absolutely bacteria-free. In the case of a tooth material destroyed by caries to a lesser extent, already a one-time application of only one solution according to the invention or one pepsin containing solution may lead to a bacteria free region of the tooth previously affected by caries.

2 Component Solution:

A 2 component system according to the present invention was prepared as follows:

|  | component A | component B |
|---|---|---|
| physical condition | liquid | liquid |
| PH | 5.5 | 2 |
| pepsin (from pig stomach) | 0.9% | — |
| NaH$_2$PO$_4$ | 1.2% | 15.6% |
| H$_3$PO$_4$ | — | <6% |
| NaOH | <0.1% | — |
| hydoxyethylcellulose (high viscosity) | 0.5% | 0.5% |
| polyethylene glycol 200 | — | 4% |
| methyl para hydroxy benzoate | 0.07% | — |
| propyl para hydroxy benzoate | 0.02% | — |

The treatment solution was prepared by mixing of component A and B at a ration of 1:3 (component A:component B), e.g. by sequentially adding the two solutions in the appropriate ration into a plastic container and thoroughly mixing the components.

The treatment solution after mixing had the following composition:

Treatment Solution:

|  | treatment solution |
|---|---|
| physical condition | liquid |
| pH | 2.1 |
| pepsin (from pig stomach) | 0.23% |
| NaH$_2$PO$_4$*2H$_2$O | 12% |
| H$_3$PO$_4$ | <5.6% |
| NaOH | <0.1% |
| hydoxyethylcellulose (high viscosity) | 0.5% |
| polyethylene glycol 200 | 3% |
| methyl para hydroxy benzoate | 0.018% |
| propyl para hydroxy benzoate | 0.005% |

Treatment Process:
a) 20 s 100 μl of treatment solution
b) rinsing
c) 20 s 100 μl of treatment solution
d) rinsing
e) 20 s 100 μl of treatment solution
f) rinsing
g) thereafter optionally filling therapy Proof of Absence of Caries:

After the enzyme solution for removing infected hard substance of the tooth in the caries lesion had been applied in accordance with the requirements, the extracted and treated tooth was air-blown and fixed in an embedding mass (cytofix, Struers company). With an internal hole saw, tooth sections through the caries lesions were made step by step. The tooth sections were freed from covering embedding material and each incubated in 1 ml live/dead dye solution for bacteria (Live/Dead BacLight, Molecular Probes company). During incubation the tooth sections were stored protected from light. With a fluorescence microscope (Zeiss company, Axioplan 2) the marked bacteria were studied under reflected light with a 24 FITC filter at an enlargement factor of 630 and 1000. While in an untreated sample under the same conditions a bacteria bed was observed, the samples treated according to the invention were absolutely bacteria-free. In the case of a tooth material destroyed by caries to a lesser extent, already a one-time application of a solution according to the invention as described above may result in a bacteria free region of the tooth previously affected by caries.

The invention claimed is:

1. Method of treating and removing carious infected dentin from a carious lesion, the method comprising the steps of:
   applying a dental composition to a site of the carious infected dentin, the composition comprising at least one biologically active protease and having a pH value of about 1 to about 4, wherein the composition is applied on the site of carious infected dentin to be treated in a volume of about 0.001 ml to about 0.5 ml; and
   allowing the composition to remain in contact with the site of the carious infected dentin for an exposure time in a range of from about 5 seconds to about 5 minutes, to digest at least a portion of the carious infected dentin from the carious lesion; wherein said dental composition comprises:
   1 to about 5,000 U/ml solvent collagenase with 1 U corresponding to the conversion of 1 mmol of L-leucine in 5 h at 37° C. and a pH of 7.5 if collagen is used as substrate,
   1 to about 45,000 U/ml solvent pepsin with 1 unit corresponding to a ΔE of 0.01 at A280 nm at 37° C. of converted hemoglobin with trichloroacetic acid (TCA), or
   10 to about 300 mAnson/ml solvent proteinase K with 1 Anson unit corresponding to 1 μmol Folin-positive amino acid at a pH of 7.5 and 35° C. if hemoglobin is used as substrate.

2. The method according to claim 1 wherein the composition has a viscosity of 10 MPas to 1000 MPas at 25° C.

3. The method according to claim 1 wherein the composition further comprises at least one glycosidase.

4. The method according to claim 1 wherein the composition further comprises at least one rheological additive.

5. The method according to claim 1 wherein the composition comprises at least pepsin and one protease inhibitor.

6. The method according to claim 1 wherein the composition further comprises one or more adjuvants comprising a complexing agent, an enzyme substrate, an enzyme effector, a thickening agent, a preservative agent, a stabilizing agent, or a combination thereof.

7. The method of claim 6 wherein the preservative agent comprises a para hydroxyl benzoic acid ester.

8. The method of claim 7 wherein the para hydroxyl benzoic acid ester comprises a methyl para hydroxyl benzoic ester, a propyl para hydroxyl benzoic acid ester, or a combination thereof.

9. The method according to claim 1 further comprising the step of identifying the carious infected dentin to be treated.

10. The method according to claim 1 further comprising the step of rinsing the treated carious infected dentin with water.

11. The method according to claim 1 wherein the dental composition comprises a first component comprising
  a protease having its proteolytic activity at a pH value of below 7,
  water,
  a buffer system providing for a pH value above the pH value at which the protease is most active, and
a second component comprising
  water,
  an acid providing for a pH value of less than or equal to the pH value at which the protease is most active; and
wherein the method further comprises mixing the first component and the second component to provide the dental composition.

12. The method according to claim 1 wherein the dental composition is applied on the site of carious infected dentin to be treated in two or more treatment steps.

13. The method of claim 1 wherein the composition further comprises one or more preservatives in an amount ranging from 0.001-1 wt.-% based on the weight of the composition.

14. The method of claim 1 wherein the composition further comprises one or more preservatives in an amount ranging from 0.01-0.25 wt.-% based on the weight of the composition.

* * * * *

UNITED STATES PATENT AND TRADEMARK OFFICE
CERTIFICATE OF CORRECTION

PATENT NO. : 9,050,332 B2
APPLICATION NO. : 12/122027
DATED : June 9, 2015
INVENTOR(S) : Ingo Haeberlein It is certified that error appears in the above-identified patent and that said Letters Patent is hereby corrected as shown below:

Title Page

Page 2, Column 1 (Other Publications)
Line 26, Delete "Kumamoylsin:" and insert -- Kumamolysin: --, therefor.

Page 2, Column 2 (Other Publications)
Line 11, Delete "pulpo-dential" and insert -- pulpo-dental --, therefor.
Line 32, Delete "Bartericidal" and insert -- Bactericidal --, therefor.
Line 38, Delete "Basidomycete" and insert -- Basidiomycete --, therefor.
Line 48, Delete "immunosupression"" and insert -- immunosuppression" --, therefor.

Specification

Column 1
Line 23, Delete "occuring" and insert -- occurring --, therefor.
Line 34, Delete "whiteish" and insert -- whitish --, therefor.

Column 6
Line 20, Delete "about," and insert -- about --, therefor.

Column 7
Line 3, Delete "methyethyl" and insert -- methylethyl --, therefor.
Line 4, Delete "methylen" and insert -- methylene --, therefor.

Column 8
Line 37, Delete "solvent" and insert -- solvent. --, therefor.

Column 10
Line 23, Delete "(ethylen" and insert -- (ethylene --, therefor.

Signed and Sealed this
Twenty-ninth Day of December, 2015

Michelle K. Lee
*Director of the United States Patent and Trademark Office*

Line 26, Delete "(ethylen" and insert -- (ethylene --, therefor.

Column 11
Line 29, Delete "may by" and insert -- may be --, therefor.

Column 14
Line 50, Delete "xanthon," and insert -- xanthone, --, therefor.
Line 51, Delete "carragen," and insert -- carrageenan, --, therefor.

Column 15
Line 61-62, Delete "the the" and insert -- the --, therefor.

Column 16
Line 18, Delete "polylysin," and insert -- polylysine, --, therefor.

Column 18
Line 10-15, Delete "hydroxid:" and insert -- hydroxide: --, therefor.
Line 22, Delete "tensides" and insert -- tensides. --, therefor.

Column 23
Line 45-50, Delete "hydoxyethylcellulose" and insert -- hydroxyethylcellulose --, therefor.
Line 54, Delete "ration" and insert -- ratio --, therefor.
Line 56, Delete "ration" and insert -- ratio --, therefor.

Column 24
Line 5-10, Delete "hydoxyethylcellulose" and insert -- hydroxyethylcellulose --, therefor.